United States Patent
Sattler et al.

(10) Patent No.: US 9,691,966 B2
(45) Date of Patent: Jun. 27, 2017

(54) SURFACE-MOUNTED COLLISION SENSOR, AND METHOD FOR COLLISION DETECTION

(71) Applicant: Siemens Aktiengesellschaft, Munich (DE)

(72) Inventors: Stefan Sattler, Forchheim (DE); Stefan Schuster, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 212 days.

(21) Appl. No.: 14/326,848

(22) Filed: Jul. 9, 2014

(65) Prior Publication Data

US 2015/0128727 A1 May 14, 2015

Related U.S. Application Data

(60) Provisional application No. 61/902,471, filed on Nov. 11, 2013.

(51) Int. Cl.
| | |
|---|---|
| *G01L 1/16* | (2006.01) |
| *H01L 41/113* | (2006.01) |
| *A61B 6/10* | (2006.01) |
| *A61B 6/00* | (2006.01) |
| *G01L 9/00* | (2006.01) |
| *H01L 41/193* | (2006.01) |

(52) U.S. Cl.
CPC .......... *H01L 41/1132* (2013.01); *A61B 6/102* (2013.01); *A61B 6/4441* (2013.01); *G01L 9/008* (2013.01); *H01L 41/193* (2013.01)

(58) Field of Classification Search
CPC .................................................. H01L 41/1132
USPC .......................................................... 73/862.68
See application file for complete search history.

(56) References Cited

U.S. PATENT DOCUMENTS

| | | | |
|---|---|---|---|
| 4,821,584 A * | 4/1989 | Lembke | B25J 19/063 |
| | | | 310/338 |
| 7,734,009 B2 | 6/2010 | Brunner et al. | |
| 7,822,464 B2 | 10/2010 | Maschke et al. | |
| 2009/0234444 A1 | 9/2009 | Maschke | |
| 2010/0114308 A1 | 5/2010 | Maschke | |
| 2010/0181871 A1* | 7/2010 | Daniel | G01L 1/16 |
| | | | 310/338 |
| 2014/0260679 A1* | 9/2014 | Baker | G01L 1/16 |
| | | | 73/862.68 |

FOREIGN PATENT DOCUMENTS

DE     G 94 03 972.0     8/1994

\* cited by examiner

*Primary Examiner* — Walter L Lindsay, Jr.
*Assistant Examiner* — Philip Marcus T Fadul
(74) *Attorney, Agent, or Firm* — Schiff Hardin LLP

(57) ABSTRACT

An apparatus assembly of a medical apparatus is equipped for collision detection by attaching a polyvinylidene fluoride (PVDF) cover assembly to at least one rigid surface of the apparatus assembly, with a resilient material between the PVDF cover assembly and the rigid surface. The PVDF assembly is composed of a PVDF foil with electrically conductive layers on opposite sides thereof. A protective layer covers the PVDF cover assembly. Electrical leads are connected to the conductive layers, and the piezoelectric property of the PVDF foil produces a voltage across the leads when a force associated with a collision acts on the PVDF foil. A detection circuit detects this voltage and initiates an appropriate response to the collision.

15 Claims, 2 Drawing Sheets

SURFACE-MOUNTED COLLISION SENSOR, AND METHOD FOR COLLISION DETECTION

RELATED APPLICATION

The present application claims the benefit of the filing date of provisional application 61/902,471, filed on Nov. 11, 2013, the content of which is incorporated herein by reference.

BACKGROUND OF THE INVENTION

Field of the Invention

The present invention concerns devices and techniques for avoiding collisions in the environment of a system having a heavy, movable component, and personnel and/or objects that are present in the environment of the system while that component may be moving. In particular; the present invention concerns avoiding such collisions between persons, including operating personnel and patients, as well as other objects that are present in an examination room in which a medical examination or procedure is being implemented using a medical apparatus that has at least one such heavy, movable component, such as a robotically-operated x-ray imaging system.

Description of the Prior Art

Medical diagnosis and intervention systems of the type used in angiography, cardiology, neurology and hybrid procedures often have relatively heavy components that are mounted, such as on a C-arm, for movement relative to a patient, so as to be positioned relative to the patient for a particular purpose, such as for obtaining a medical image of the patient. For conventional two-dimensional imaging, the components of the imaging apparatus can be positioned by respective motor drives in a flexible manner around the patient lying on a patient bed or patient table. For 3D imaging, these components can be driven automatically or semi-automatically around the patient, in order to acquire a larger number of individual images that are necessary for the 3D image reconstruction.

In addition to x-ray mounting arrangements, such as floor-mounting and ceiling-mounted brackets with articulated arms, it has become increasingly popular to employ robots of the type used for industrial purposes in order to position a C-arm, on which components such as an x-ray source and a radiation detector are mounted, relative to the patient. These types of robotically-operated imaging systems allow for high-precision positioning and kinematics. Such robots typically exhibit multi-axis kinematics, and the increase in the degrees of freedom of movement of the overall system increase the requirements for safety in the environment in which such systems are operated. Particularly in environments wherein human/robot collaboration exists (i.e., humans and the robot are both moving in the same room and with respect to a common focus, namely the patient), the possibility of one of the moving, heavy components coming into contact with a human, either the patient or attending personnel, exists, and steps must be taken to avoid injuries due to such potential collisions.

There is also a risk that the moving component may collide with an object within its movement range, thereby damaging the component or the object, or both.

In workspaces of the type described above, it is generally not possible to install protective devices that would physically separate humans in the environment from a collision with a component moved by the robot. Therefore, other protective measures are known in order to detect the possibility of a collision occurring, and to continually minimize this possibility via the robot controller, such as by reducing the speed of movement when the components moved by the robot controller are in proximity to the patient table.

Since contact between personnel/objects and moving objects can occur anywhere in an operating room environment and at any time, a risk of collision remains, despite the use of known collision-detection techniques. In order to minimize this risk as much as possible, it would be desirable to have a collision-detection technology in place that is effective for avoiding collision between personnel/objects and all portions of all surfaces of components or assemblies that, when moving, would present a risk of injury to such personnel. This requires a sensor technology that is "surface-covering," meaning that sensing capability is provided over the entire surface of any component or assembly that presents a risk of injury due to a collision.

In addition to the requirements imposed by the industry standard for robots (DIN EN ISO 10218, Parts 1 and 2, Medicine Standard IEC 60601-1, $3^{rd}$ Edition, namely the "first fault safety" described therein), such as sensor technology must take into account the technically feasible solutions and be capable of differentiation among various injury classes (for example, according to the AIS 98 Code, Abbreviated Injury Scale).

Current angiography systems, for example, typically have different integrated collision protection mechanisms that can include stored software models, electronic permission buttons (DMG, Dead Man Grip) and additional protective measures. Examples of such known collision-detection mechanisms and measures are as follows.

Collisions at resiliently-mounted housing parts of the C-arm radiation source/detector can be detected by the triggering of electronic buttons that are situated on those components. Such an approach is described in U.S. Pat. No. 6,550,964.

Electrical signal-generating, pressure-sensitive bumpers can be attached to the profile of the C-arm, which function as resistive switching elements. These types of bumpers emit a signal when a relatively strong deformation of the pressure-sensitive bumper occurs, and this signal is supplied to a control circuit for analysis and evaluation for collision detection and avoidance. Such a pressure-sensitive bumper is described in German Utility Model DE 9403972 U1.

Another known approach is described in U.S. Pat. No. 5,570,770 wherein the motor current supplied to actuators of drive motors, which move various components in an x-ray examination room, is monitored in order to detect that a collision has taken place.

In general, it is also known to locate acceleration sensors and/or force sensors, such as strain gauges, magnetic field sensors, etc., at appropriate locations on respective components in order to provide signals that can be used for collision detection.

A disadvantage that all of these known approaches have in common is that they are difficult to integrate into the covering of a surface, particularly complexly-shaped surfaces of parts of a medical apparatus, in a cost-effective manner, while still maintaining reliable collision detection. For example, the aforementioned pressure-sensitive bumpers, which emit an electrical signal when strongly deformed, can be used individually and locally only to a limited extent, due to the geometry of such bumpers. Moreover, such known pressure-sensitive bumpers provide the most reliable emission of a signal when the force (impact) applied thereto occurs substantially perpendicularly to the pressure-sensitive surface of the bumper. Impact angles that are greater than 45° can lead to an erroneous response. Moreover, such bumpers usually are not able to detect collisions that occur within a few millimeters from the edges of the bumper. When such bumpers have been attempted to be used to provide coverage over a relatively large area, a large number of individual pressure-sensitive bumpers are connected together on the surface of the component in question, and are covered with foam, and the surface is then subsequently finished with a highly flexible lacquer. The lacquered foam coating is very expensive, and is subject to being damaged by sharp articles.

With regard to the approach involving resiliently mounted housing parts, such housing parts must be able to function in any spatial support/orientation, and in response to any desired movement acceleration. This means that such parts can have only a predetermined maximum weight, otherwise the restoring force on the housing thereof would be too large in order to trigger a detection in the event of a collision. Moreover, such buttons each detect movement along a particular direction. Because collision with such a housing can occur from many different directions, detection must be ensured in all directions, and this can be realized only by using a very complex and mechanically delicate and expensive configuration.

Moreover, separation lines, such as produced by edges and grooves, must be provided in order to achieve this movement detection, and sterilization and hygienic problems can result from the presence of such crevices in a medical environment.

Membranes made of polyvinylidene fluoride (PVDF) are known for many different purposes in many different fields. PVDF membranes are known, for example, for use as pressure-sensors when stretched over a surface with an underlying clearance beneath the membrane, in the manner of a drumhead stretched over the surface. Such a clearance beneath the PVDF membrane is necessary in such arrangements in order to permit the membrane to be deformed by a sufficient amount so as to detect and measure the applied pressure. PVDF membranes are also known for use in a manner similar to stream gauges. Known problems associated with PVDF membranes designs are the implementation of large-area elements, applications with large force impacts, and exposure to sharp articles. When PVDF membranes have been used in the context of a pressure-based design, they typically exhibit only a small dynamic range, and this range is strongly dependent on the supporting structure for the membrane, because only a mechanical change of the film in terms of its thickness can be detected in order to provide the relevant signal.

PVDF is a semi-crystalline plastic that is known to be piezoelectric, i.e., it can produce an electrical signal when subjected to a deformation. Such material is known for use as an acoustic sensor, such as in a microphone, as well as an acoustic actuator, such as in a speaker. PVDF membranes are also known for use in certain controlled electromechanical systems, such as in force-regulated piezo-servo motors. In medical technology, ultrasound heads are known that make use of PVDF film to not only emit the ultrasound signal, but also to receive the reflected signal.

SUMMARY OF THE INVENTION

An object of the present invention is to provide a sensor technology for collision-detection for use in environments of the type described above, wherein the disadvantages of the aforementioned known technologies are avoided or minimized.

This object is achieved in accordance with the present invention by an apparatus assembly that is part of a medical apparatus and that is mounted for movement in a medical examination environment in a manner that exposes persons or objects in the vicinity of the movement of the apparatus assembly to the risk of injury due to a collision with the apparatus assembly, wherein a surface of the apparatus assembly is covered, substantially completely, by a PVDF cover assembly that includes a PVDF foil with a conductive layer disposed on opposite sides of the PVDF foil. The apparatus assembly according to the invention is based on the insight that the piezoelectric property of PVDF can be exploited for use as a collision-detection sensor, when a PVDF cover assembly of this type is appropriately attached to the surface of the apparatus assembly, and is protected from damage by an exterior coating.

As used herein, the term "apparatus assembly" can include only one component (i.e., a "stand alone" component) or an assembly of multiple components that move together as a group.

Because the PVDF foil can be made to conform even to a surface with a complex profile such as an irregularly shaped individual component or a combination of assembled components, the PVDF foil, and thus the PVDF cover assembly, in accordance with the invention forms a single, uninterrupted assembly that covers the relevant surface or surfaces of the apparatus assembly completely, with no gaps and no overlapping of multiple individual covers.

In accordance with the invention, a resilient or elastic layer, such a foam layer, is situated between the surface of the apparatus assembly in question, and one of the conductive layers of the PVDF cover assembly. The conductive layer on the opposite side of the PVDF cover assembly (i.e., on the opposite side of the PVDF film or foil) is covered with a protective coating that is resistant to piercing and other types of damage that typically represent a risk of impairing the ability of the PVDF cover assembly to reliably emit an electrical signal.

In a further embodiment, two such PVDF cover assemblies can be situated one above the other between the resilient material that is on the surface of the component, and the exterior protective coating. The use of two such PVDF cover assemblies provides redundancy in detecting collisions, as well as providing a higher likelihood that even if one of the PVDF cover assemblies is damaged, the other will still remain functional.

The invention also encompasses a medical examination apparatus having such an apparatus assembly as one of the examination or therapy assemblies thereof that is covered by a PVDF cover assembly as described above.

The present invention also encompasses a method for collision detection wherein potential collisions in an environment of the type described above are monitored and detected by an apparatus assembly covered with a PVDF cover assembly as described above, and appropriate countermeasures are then taken if and when a collision is detected.

The method according to the invention can also include, in a further embodiment, a self-test, wherein the electrodes of PVDF cover assembly are periodically provided with a reference signal, such as a square wave at an appropriate frequency, which produces a known response from the PVDF cover assembly, as long as the PVDF cover assembly is intact and functioning properly. When such a test signal fails to produce the expected response, it is assumed that damage to the PVDF cover assembly has occurred, and an appropriate warning or alarm can then be generated.

DESCRIPTION OF THE PREFERRED EMBODIMENTS

Figure 1:
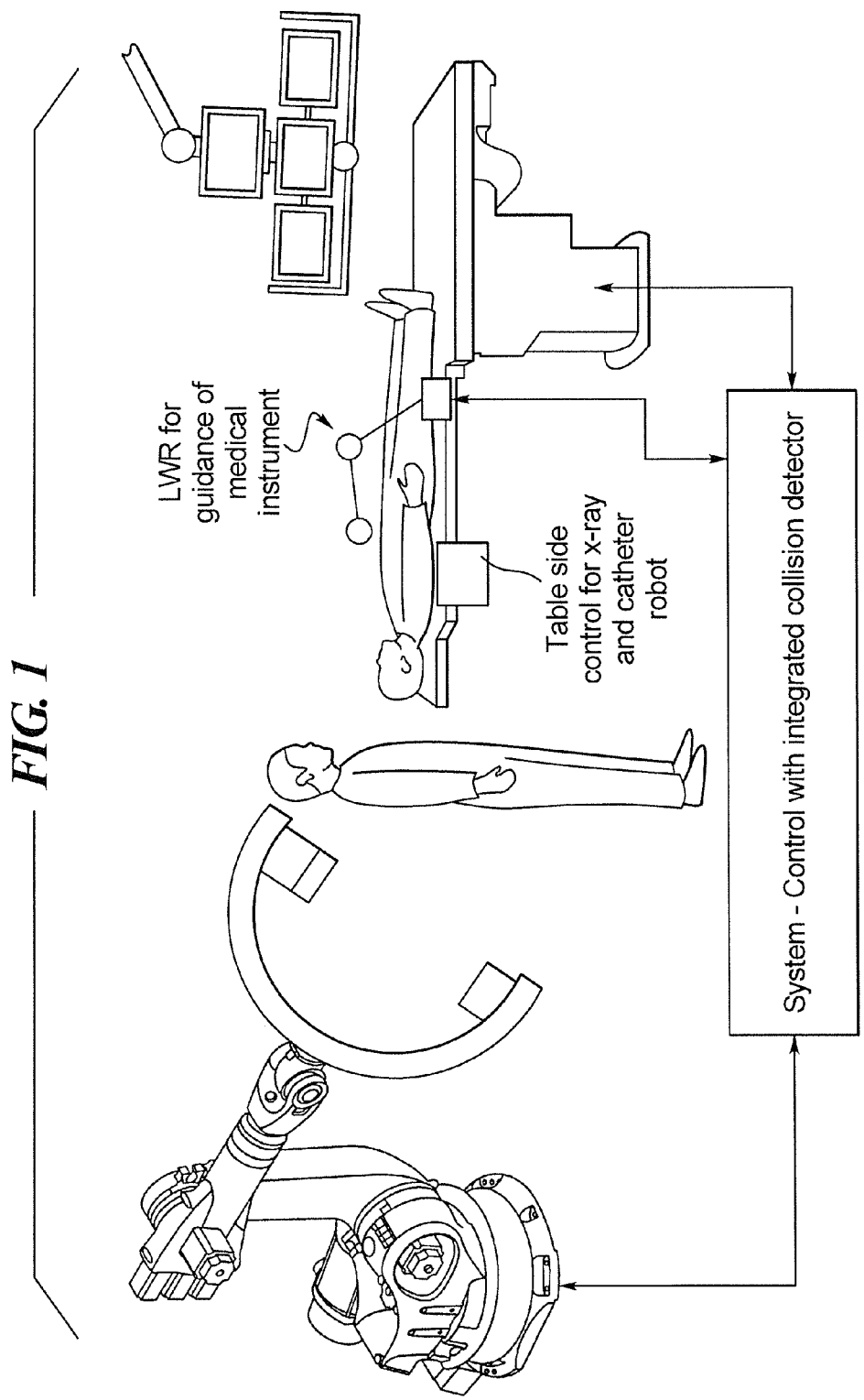
FIG. 1 schematically illustrates a medical examination environment in which the collision-detection technology in accordance with the present invention can be implemented.

FIG. 1 schematically illustrates an environment in which the collision sensor in accordance with the present invention is suitable for use. In the example shown in FIG. 1, this environment is a medical examination or operating room in which a robotically-operated x-ray imaging system, shown at the left in FIG. 1, is moved relative to an attendant or a physician (shown standing in the center of FIG. 1) so as to obtain medical images of a patient lying on a patient table. The examination may include the use of a lightweight robot LWR, for guidance of a medical instrument. Display screens are shown at the right in FIG. 1, and the patient table, as is known, has a side control for the x-ray imaging system and for the catheter robot. All components are operated by a system control, which has an integrated collision detector. The collision detector is explained in further detail below, and provides electrical signals indicating the occurrence of a collision between any of the components or assemblies thereof, and particularly collisions of an apparatus assembly of the robotically operated x-ray imaging system with any humans in the environment. Other than the collision detector in accordance with the present invention, the components shown in FIG. 1 are well known to those of ordinary skill in the field of medical imaging, and operate in a conventional manner.

Figure 2:
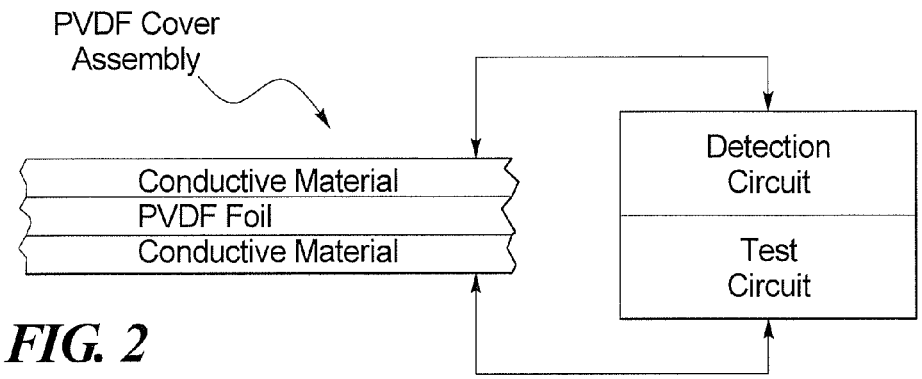
FIG. 2 is a sectional view through a PVDF cover assembly in accordance with the present invention.

For collision detection, a PVDF (polyvinylidene fluoride) cover assembly in accordance with the present invention, as shown in FIG. 2, is utilized. The PVDF cover assembly is composed of a PVDF foil, with respective conductive layers on opposite sides thereof. The piezoelectric property of the PVDF foil causes the foil to generate an electrical signal between the conductive layers, which serve as electrodes, when the PVDF foil is deformed by a force impacting on the PVDF foil through one of the conductive layers. This signal is supplied to a detection circuit as shown in FIG. 2, which can be incorporated in the system control shown in FIG. 1.

Because the PVDF foil can be used as a surface-wide covering for a component or combination of components having virtually any exterior shape, the PVDF cover assembly including such a PVDF foil can be used to completely cover the C-arm portion of the robotically operated x-ray image system shown in FIG. 1, including the x-ray source and/or the x-ray detector thereof. Additionally, such a PVDF cover assembly can be used to cover as much of the robot itself as may be desired.

If and when a surface covered with the PVDF cover assembly comes into contact with an animate or inanimate object, such as personnel in the environment shown in FIG. 1, the aforementioned electrical signal will be provided to the detection circuit and appropriate conventional steps can then be taken in response. Such steps, for example, may include the immediate stoppage of all movement of the robotically operated x-ray imaging system.

As also shown in FIG. 2, the conductive layers of the PVDF cover assembly may be connected to a test circuit, in order to continually monitor the proper functioning of the PVDF assembly. This can be implemented by emitting a short test pulse cyclically (such as using a millisecond clock cycle, for example). This leads to a contraction of both of the conductive layers, and thus produces a known response signal as a reaction. Even slight damage to the PVDF cover assembly, and more specifically the PVDF foil thereof, can be discovered with this technique, since the reaction signal in the event of such damage will deviate from the expected value in the read-back channel.

The test signal can be a high-frequency square wave signal, which will result in a returned signal after a slight time delay. Any amplitude change in the returned signal can be ascribed to a drop-off of the piezoelectric effect of the PVDF foil. There can be various causes for this, such as chemical variations, mechanical destruction of the foil, or a material modification due to radiation by x-rays and/or temperature influences. A change in the time curve (i.e., the step response to the square wave signal) also can be ascribed to a defect of the PVDF foil. If and when a return signal indicates the existence of a fault, the test circuit can initiate an appropriate response, such as a warning or alarm.

Figure 4:
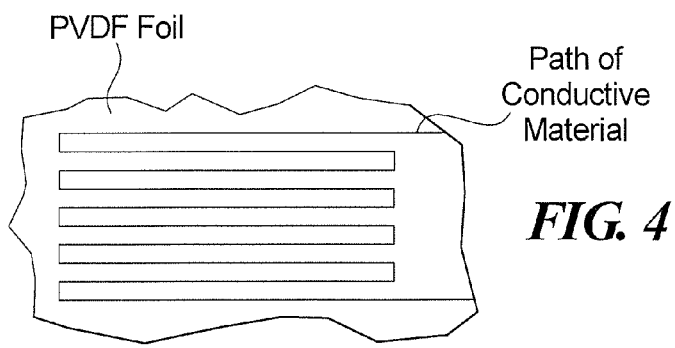
FIG. 4 shows an embodiment of a configuration of the conductive path of one of the conductive layers of the PVDF cover assembly shown in FIG. 2.

The effectiveness of such testing can be further enhanced in an embodiment as shown in FIG. 4, wherein the conductive layers are designed not as a closed area (plate-type electrode) but rather in the form of a meandering path. An example of such a meandering path is shown in FIG. 4, but any appropriate type of meandering path can be used. By the use of such a path of the conductive layer, it can be assumed that this path will very likely be interrupted given damage to the PVDF foil, and this aforementioned differing reaction signal will occur.

Figure 3:
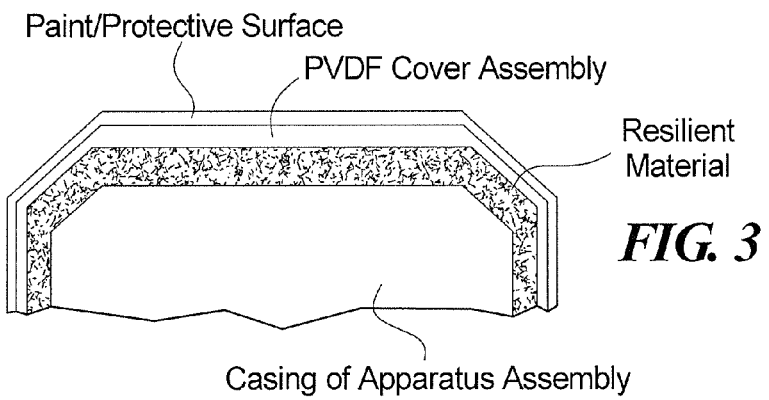
FIG. 3 is a sectional view through a first embodiment of an apparatus assembly having a PVDF cover assembly thereon in a mounting/attachment arrangement in accordance with the present invention.

The substructure for attaching the PVDF cover assembly to the surface of an apparatus assembly to be protected is shown in FIG. 3, in a first embodiment. In this embodiment, the cover or housing or casing of each component of the apparatus assembly in question (or at least the portion thereof that is exposed so as to present a collision risk) is covered with a flexible substrate. In the case of an assembly composed of multiple components, the flexible substrate and the PVDF cover assembly form an uninterrupted sheet that extends without gaps over any gaps or interstices that may be present between individual components in the assembly. The flexible substrate may be a thin layer of silicone, foamed material, or other elastomers. The sensitivity and the linearity of the output signal of the PVDF cover assembly, and thus the robustness of the overall structure, is thereby increased.

The PVDF cover assembly as shown in FIG. 2 covers the flexible substrate, and is in turn covered at the exterior with a protective surface and/or paint. The protective surface is a suitable material that resists piercing, tearing, or other types of aberrational impacts that can damage the PVDF cover assembly, and specifically the PVDF foil thereof. The electrical contacts to the conductive layers can proceed through the protective surface and/or through the flexible substrate, or may be made at any location between those items.

In general, the PVDF cover assembly and the mounting thereof in accordance with the invention take place with items in the following sequence, from bottom-to-top in the orientation shown in FIG. 3: a stable foundation (here the casing or casings of one or more components of the apparatus assembly), a flexible layer covering a large area of the stable foundation, an electrically conductive surface that is substantially coextensive in area with the flexible layer, a PVDF film that is also substantially coextensive with the electrically conductive surface, another electrically conductive surface that is substantially coextensive the PVDF film and the aforementioned electrically conductive surface, a protective layer, and a coating or paint.

Generally, the flexible layer can have a thickness as thin as 2 mm or less, but thicker images may be used as needed.

Figure 5:
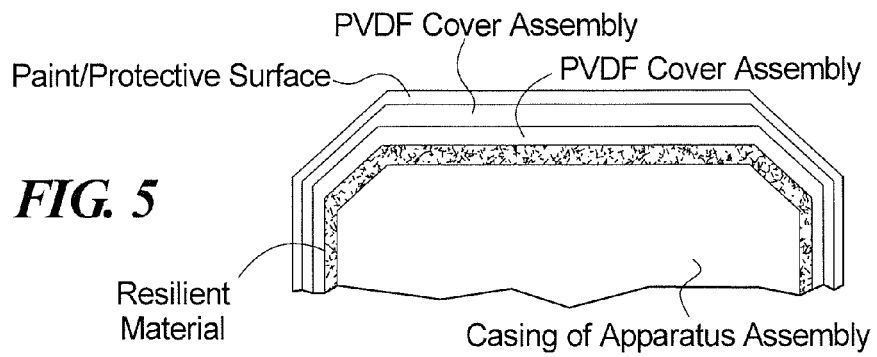
FIG. 5 is a section, in a further embodiment of the invention, through an apparatus assembly having multiple PVDF cover assemblies in accordance with the present invention.

In a further embodiment shown in FIG. 5, two PVDF cover assemblies are situated between the paint/protective surface, and the flexible substrate. Each of the PVDF cover assemblies in FIG. 5 can function independently, and provide respective signals to the detection circuit, thereby providing redundant reliability for detecting collisions. Moreover, each of the PVDF cover assemblies in FIG. 5 can be individually tested with the aforementioned self-test.

It may also be desirable to provide each PVDF cover assembly with its own, dedicated detection circuit and/or test circuit. Nevertheless, since only one film will ever be excited with the test signal, a more precise read-back capability of the reaction signal is a further advantage of this embodiment.

For jerky collisions as most frequently occur, the embodiment shown in FIG. 3 is sufficient, and satisfies the requirements associated with the aforementioned "first fault safety" of the relevant requirements for medical technology. Since the evaluation electronics in the detection circuit can never be constructed with ideal properties, the evaluation electronics will always consume a certain amount of current at the measurement input thereof, which thus results in a "subtraction" from the actual voltage that is produced by the collision. Therefore, the use of redundant PVDF cover assemblies providing respective signals to a single detection circuit can be of advantage in order to detect smaller collision forces.

Although modifications and changes may be suggested by those skilled in the art, it is the intention of the inventors to embody within the patent warranted hereon all changes and modifications as reasonably and properly come within the scope of their contribution to the art.

We claim as our invention:

1. A collision detection arrangement, comprising:
   an apparatus assembly of a medical apparatus, said apparatus assembly comprising at least one rigid surface that, when said apparatus assembly is moving in an environment in which at least one animate or inanimate object is present, is susceptible to collision with said object;
   a resilient material, said resilient material having a first material surface in direct surface-to-surface touching contact with said at least one rigid surface over substantially an entirety of said at least one rigid surface, and a second material surface opposite said first material surface;
   a single, uninterrupted polyvinylidene fluoride (PVDF) cover assembly in direct contact with said resilient material and covering substantially an entirety of said resilient material and said at least one surface;
   said PVDF cover assembly comprising a PVDF foil having a first side, and a second side opposite said first side, and a first conductive layer between said first side of said PVDF foil and said resilient material, and a second conductive layer on said second side of said PVDF foil, said first conductive layer having a layer surface in direct surface-to-surface touching contact with said second material surface over substantially an entirety of said resilient material;
   a first electrical lead connected to said first conductive layer and a second electrical lead connected to said second conductive layer, said PVDF foil being piezoelectric and, when subjected to a force associated with said collision applied anywhere over the entirety of said at least one rigid surface of said apparatus assembly, producing a voltage across said first and second electrical leads; and
   a pierce-resistant protective layer having an interior surface covering substantially an entirety of said second conductive layer and having an exterior surface at which said collision and said force occur, thereby placing said pierce-resistance protective layer between said collision and said at least one rigid surface.

2. An arrangement as claimed in claim 1 comprising a detection circuit connected to said first and second electrical leads, said detection circuit being configured to identify an occurrence of a collision of said moveable apparatus assembly with said at least one object, dependent on said voltage across said leads.

3. An arrangement as claimed in claim 1 comprising a test circuit connected across said first and second electrical leads, said test circuit being configured to repeatedly emit a test signal to one of said first and second conductive leads and to evaluate a response signal, which occurs in response to said test signal, at the other of said first and second electrical leads, in order to verify that said PVDF foil is intact.

4. An arrangement as claimed in claim 1 wherein said resilient material has a thickness of 2 mm or less.

5. An arrangement as claimed in claim 1 wherein said PVDF cover assembly is a first PVDF cover assembly, and wherein said arrangement comprises a second PVDF cover assembly, identical to said first PVDF cover assembly, disposed between said resilient material and said protective layer, adjacent said first PVDF cover assembly.

6. An arrangement as claimed in claim 5 comprising a single detection circuit connected to said first and second electrical leads of both said first and second PVDF cover assemblies, said detection circuit being configured to identify an occurrence of a collision of said apparatus assembly with said at least one object, dependent on respective voltages across said leads.

7. An arrangement as claimed in claim 5 comprising first and second detection circuits respectively connected to said first and second electrical leads of said first and second PVDF cover assemblies, said detection circuits each being configured to identify an occurrence of a collision of said apparatus assembly with said at least one object dependent on the voltage across the leads respectively connected thereto.

8. A medical apparatus comprising:
   a plurality of apparatus assemblies configured to implement a medical examination or therapy;
   said plurality of apparatus assemblies including a moveable apparatus assembly, said movable apparatus assembly comprising at least one rigid component surface that, when said apparatus assembly is moving in an environment in which at least one animate or inanimate object is present, is susceptible to collision with said object;

a resilient material, said resilient material having a first material surface in surface-to-surface contact with said at least one rigid surface over covering substantially an entirety of said at least one rigid surface, and a second material surface opposite said first material surface;

an uninterrupted polyvinylidene fluoride (PVDF) cover assembly in direct contact with said resilient material and covering substantially an entirety of said resilient material and said at least one surface;

said PVDF cover assembly comprising a PVDF foil having a first side, and a second side opposite said first side, and a first conductive layer between said first side of said PVDF foil and said resilient material, and a second conductive layer on said second side of said PVDF foil, said first conductive layer having a layer surface in direct surface-to-surface touching contact with said second material surface over substantially an entirety of said resilient material;

a first electrical lead connected to said first conductive layer and a second electrical lead connected to said second conductive layer, said PVDF foil being piezoelectric and, when subjected to a force associated with said collision applied anywhere over the entirety of said at least one rigid surface of said apparatus assembly, producing a voltage across said first and second electrical leads; and a pierce-resistant protective layer having an interior surface covering said second conductive layer and having an exterior surface at which said collision and said force occur, thereby placing said pierce-resistance protective layer between said collision and said at least one rigid surface.

9. A medical apparatus as claimed in claim 8 comprising a detection circuit connected to said first and second electrical leads, said detection circuit being configured to identify an occurrence of a collision of said apparatus assembly with said at least one object, dependent on said voltage across said leads.

10. A medical apparatus as claimed in claim 8 comprising a test circuit connected across said first and second electrical leads, said test circuit being configured to repeatedly emit a test signal to one of said first and second conductive leads and to evaluate a response signal, which occurs in response to said test signal, at the other of said first and second electrical leads, in order to verify that said PVDF foil is intact.

11. A medical apparatus as claimed in claim 8 wherein said resilient material has a thickness of 2 mm or less.

12. A medical apparatus as claimed in claim 8 wherein said PVDF cover assembly is a first PVDF cover assembly, and wherein said cover comprises a second PVDF cover assembly, identical to said first PVDF cover assembly, disposed between said resilient material and said protective layer, adjacent said first PVDF cover assembly.

13. A medical apparatus as claimed in claim 12 comprising a single detection circuit connected to said first and second electrical leads of both said first and second PVDF cover assemblies, said detection circuit being configured to identify an occurrence of a collision of said apparatus assembly with said at least one object, dependent on respective voltages across said leads.

14. A medical apparatus as claimed in claim 12 comprising first and second detection circuits respectively connected to said first and second electrical leads of said first and second PVDF cover assemblies, said detection circuits each being configured to identify an occurrence of a collision of said apparatus assembly with said at least one object, dependent on the voltage across the leads respectively connected thereto.

15. A method for collision detection between an apparatus assembly of a medical apparatus and at least one animate or inanimate object in an environment of the apparatus assembly, said apparatus assembly comprising at least one rigid surface that, when said apparatus assembly is moving in an environment in which said at least one object is present, is susceptible to collision with said object, said method comprising:

covering substantially an entirety of said at least one rigid surface with a resilient material, so as to place a first material surface of said resilient material in direct surface-to-surface touching contact with said at least one rigid surface, said resilient material having a second material surface opposite said first material surface;

attaching an uninterrupted polyvinylidene fluoride (PVDF) cover assembly in direct contact with said resilient material and covering substantially an entirety of said resilient material and said at least one rigid surface;

forming said PVDF cover assembly to comprise a PVDF foil having a first side, and a second side opposite said first side, and a first conductive layer between said first side of said PVDF foil and said resilient material, and a second conductive layer on said second side of said PVDF foil, so as to place a layer surface of said first conductive layer in direct surface-to-surface touching contact with said second material surface over substantially an entirety of said resilient material;

connecting a first electrical lead said first conductive layer and connecting a second electrical lead connected to said second conductive layer, said PVDF foil, when subjected to a force associated with said collision applied anywhere over the entirety of said at least one rigid surface of said apparatus assembly, producing a voltage across said first and second electrical leads;

covering said second conductive layer with an interior surface of a pierce-resistant protective layer that has an exterior surface at which said collision and said force occur, thereby placing said pierce-resistance protective layer between said collision and said at least one rigid surface; and electrically detecting and evaluating said voltage as an indication that a collision has occurred at said at least one rigid surface between said apparatus assembly and said at least one object.

* * * * *